United States Patent
Feucht et al.

(10) Patent No.: US 6,171,867 B1
(45) Date of Patent: Jan. 9, 2001

(54) PIEZOELECTRIC GAS SENSOR

(75) Inventors: Gernot Feucht, Mutterstadt; Andreas Schleicher, Einhausen; Georg Frank, Hofheim, all of (DE)

(73) Assignee: Ticona GmbH, Frankfurt (DE)

( * ) Notice: Under 35 U.S.C. 154(b), the term of this patent shall be extended for 0 days.

(21) Appl. No.: 08/378,838

(22) Filed: Jan. 26, 1995

(30) Foreign Application Priority Data

Jan. 29, 1994 (DE) ................................................. 44 02 671

(51) Int. Cl.$^7$ ........................... G01N 33/00; G01N 29/02
(52) U.S. Cl. ........................... 436/124; 73/24.01; 422/83; 422/88; 436/127; 436/135; 436/149
(58) Field of Search ................................. 422/82.01, 83, 422/88; 73/24.06, 24.01; 310/313 B, 313 D, 313 R; 436/149, 124, 127, 135

(56) References Cited

U.S. PATENT DOCUMENTS 5,423,902 * 6/1995 Strutz et al. ............................ 95/273

FOREIGN PATENT DOCUMENTS

4314734 * 11/1994 (DE).

OTHER PUBLICATIONS

AN 1985: 546376 HCA Plus Fog, Henrik M. (Abstract Only).*
Chimia, Bd. 28, No. 9, Sep. 1974, pp. 567–575, by Von R. Gabler entitled "Neue Polyphenylensulfonie Reacktionen an Festen Polymeren".

Fog et al., "Piezoelectric Crystal Detector for the Monitoring of Ozone in Working Environments", *Anal. Chem.*, vol. 57(13), pp. 2634–2638 (1985).

Chemical Abstracts CA104(24):218317w, Abstract of JP 84–123975, published Jan. 9, 1986.

* cited by examiner

*Primary Examiner*—Arlen Soderquist
(74) *Attorney, Agent, or Firm*—Frommer Lawrence & Haug

(57) ABSTRACT

The invention relates to a sensor comprising a piezoelectric crystal with a polyarylene thioether-containing coating, the coating containing at least one polyarylene system having repeating units of the formula I,

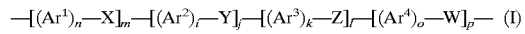

which contain at least one thioether group, in which $Ar^1$, $Ar^2$, $Ar^3$ and $Ar^4$ are identical or different aryl systems having from 6 to 18 carbon atoms, W, X, Y and Z are identical or different linking groups, selected from the group comprising —$SO_2$—, —S—, —SO—, —O—, —CO—, —$CO_2$—, alkylene or alkylidene having from 1 to 6 carbon atoms and —$NR_1$—, where $R^1$ is an alkyl or alkylide group having from 1 to 6 carbon atoms and at least one linking group must be —S—, n, m, i, j, k, l, o, p are, equal or different, integers zero, 1, 2, 3 or 4, their sum having to be at least 2, and to the use thereof.

20 Claims, No Drawings

PIEZOELECTRIC GAS SENSOR

It is known (JP 84-123975), that conductivity sensors comprising polyphenylene sulfide with Au electrodes can be used for detecting extremely reactive gases such as $SO_2F_2$ and $SOF_2$. In the process, $SO_2$ is incorporated into the polymer with the formation of chain cross-links. The concomitant conductivity change is detected. This sensor cannot be used, however, to detect ozone, halogen or peroxide-containing compounds. A problem with this principle is the corrosion resistance of the Au electrodes with respect to the gases to be detected.

It is known (Anal. Chem., 57(13), 2634-8, 1985) that ozone can be detected by means of a piezoelectric 1,4-polybutadiene-coated sensor. A drawback with this sensor is the preparation of the polymer coating by brush application, it being possible for the surface of the contacting means to be damaged in the process. The homogeneity of the layer likewise is not reproducible by these processes, as is confirmed by the greatly fluctuating frequency change range reported of from 2000 to 10000 Hz. Moreover, the observed frequency changes due to the absorbed amounts of ozone in the ppb range are very small.

It is known that electronic frequency generators for generating oscillations make use of a piezoelectric element made of quartz or lead/zirconium titanate ceramics. One of the resonance frequencies is selected for detecting changes in mass and is amplified by an additionally connected external frequency generator.

It is known that the relationship between fundamental mode (period T) and mass m of the harmonic oscillator then is as follows:

$$T = 2\pi \sqrt{\frac{m \cdot s}{K}} \quad (1)$$

where s is the displacement and K is the restoring force of the oscillating mass. It is then true, owing to the relationship between vibrational frequency and vibrational amplitude, that $$F^2 = 1/T^2 = \text{const}/m \quad (2)$$

Equation (2) therefore shows that an increase in the oscillating mass, e.g. by chemisorption processes, results in a frequency shift of the resonance frequency of the piezoelectric material.

The expression const in equation (2) represents material constants (acoustic impedance, shearing modulus) of the piezoelectrically active material.

In the case of quartz, for example, the following function results for the frequency change $\Delta f$:

$$\Delta f = -2.3 \cdot 10^6 \cdot F^2 \cdot m/A \quad (3)$$

in which A is the vibrating surface, F is the fundamental mode and $\Delta m$ is the change in mass.

If the vibrating surface (e.g. a quartz disk) is provided with a coating, the frequency of the system changes, owing to the increase in mass, in accordance with equation (3).

If the coating has absorbent properties with respect to one or more substances in the ambient medium, the vibrating system responds by a change in frequency to any absorption taking place. The characteristics of the sensor (selectivity, sensitivity, regenerability, cumulability) can be adjusted within wide limits by suitable selection of the absorber.

The object of the invention is to provide a sensor for the detection of ozone, halogen and peroxide-containing compounds, which is corrosion-resistant, can be fabricated in a reproducible manner, has a high absorbency and rapidly converts the gases to be detected into a non-volatile compound.

It was found, surprisingly, that the abovementioned drawbacks are overcome and the desired characteristics are obtained by the use of polyarylene thioethers on piezocrystals, suitable coating and aftertreatment techniques being employed. Thus detectors are obtained for the quantitative detection of halogens, peroxide-containing compounds and ozone.

The invention relates to a sensor comprising a piezoelectric crystal with a polyarylene thioether-containing coating.

Polymers which can be used for the purposes of the invention are polyarylene systems having repeating units of the formula I, which contain at least one thioether group,

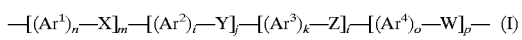

in which

Ar$^1$, Ar$^2$, Ar$^3$ and Ar$^4$ are identical or different aryl systems having from 6 to 18 carbon atoms, W, X, Y and Z are identical or different linking groups, selected from the group comprising —SO$_2$—, —S—, —SO—, —O—, —CO—, —CO$_2$—, alkylene or alkylidene having from 1 to 6 carbon atoms and —NR$^1$—, where R$^1$ is an alkyl or alkylide group having from 1 to 6 carbon atoms and at least one linking group must be —S—, n, m, i, j, k, l, o, p are, equal or different, integers zero, 1, 2, 3 or 4, their sum having to be at least 2. The arylene systems are simple arylenes such as phenylene or naphthalene or arylene systems directly linked via para, meta or ortho positions, such as biphenylene.

Polymers preferably used for the invention are polyarylenes having repeating units of the formulae (II–VIII):

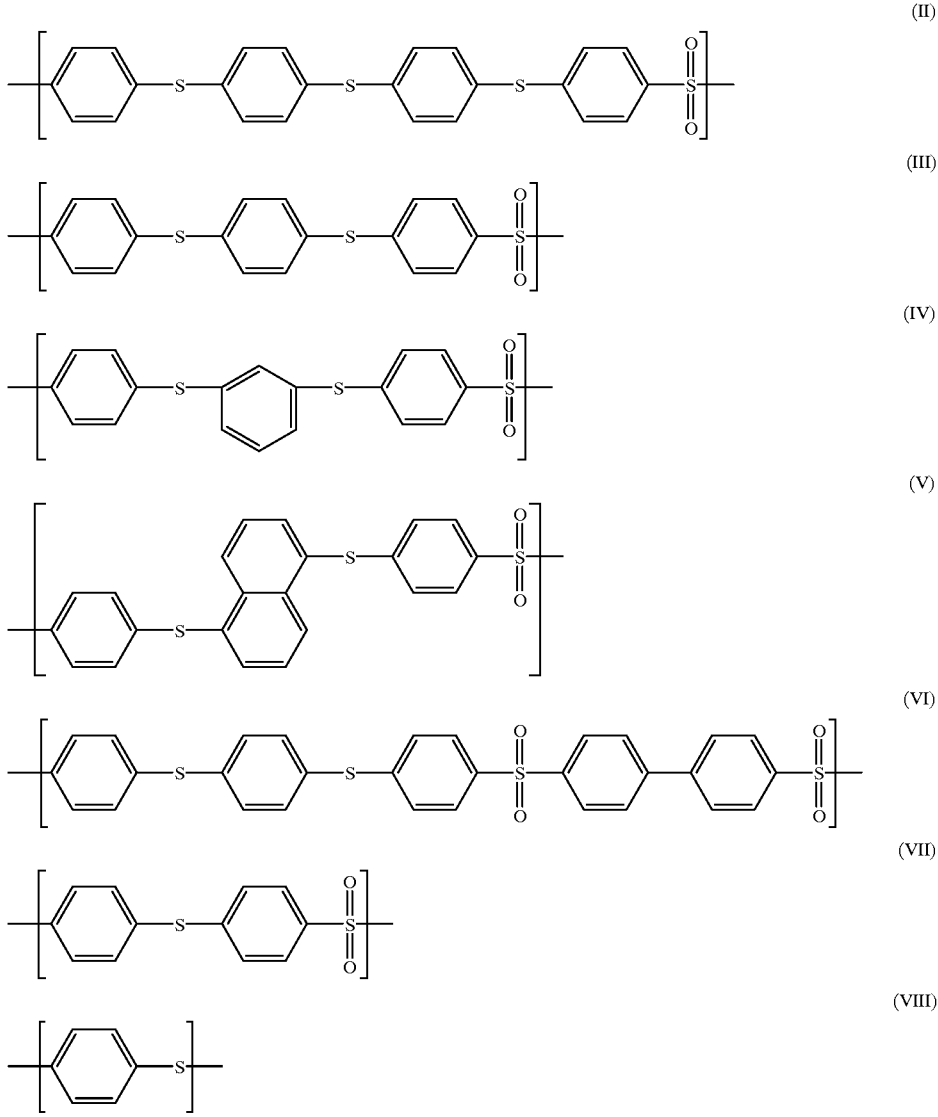

Particular preference is given, according to the invention, to the polyphenylene sulfides (PPS) having repeating units of the formula (VIII). The syntheses of the polyarylenes having repeating units of the formula II–VI are described in Chimia 28 (9), 567, those of the polyarylenes having repeating units of the formula VII is described in U.S. Pat. No. 4,016,145, and those of the polyarylenes having repeating units of formula VIII is described in U.S. Pat. No. 3,919,177, U.S. Pat. No. 4,038,262 and U.S. Pat. No. 4,282,347.

Suitable for the invention are linear and branched polyarylene systems having repeating units of the formula I, which have a mean molecular weight of from 10,000 to 200,000, preferably a molecular weight of from 15,000 to 150,000. It is also possible to use mixtures of different polyarylene systems having repeating units of the formula I.

According to the invention, any crystals can be used which exhibit a piezoelectric effect.

Preference is given, for the purpose of the invention, to inorganic piezoelectric crystals such as alkaline earth metal titanates, lead-zirconium titanates and quartzes, particular preference being given to alkaline earth metal titanates, especially barium titanate, and quartz.

For the purposes of the invention it is possible to employ piezoelectric crystals which have their fundamental mode in a frequency range of from 20 kHz to 100 MHz, preferably from 0.1 MHz to 50 MHz, and especially preferably from 0.1 MHz to 30 MHz. Alternatively it is possible to employ, for the detection, harmonics whose frequencies are in a frequency range from 1 MHz to 1000 MHz, preferably from 30 MHz to 500 MHz.

According to the invention, the polyarylene thioether can be applied, by means of general coating methods, to the piezocrystals unilaterally or bilaterally. Preference is given in this context to coating methods which are based on polymer or monomer solutions, e.g. spin-coating, dip-coating or spray methods. Suitable solvents comprise all organic substances which dissolve the polymer or monomer in question in sufficient concentrations, for example caprolactam, 1-chloronaphthalene, 1-methoxynaphthalene, isoquinoline, 2-methoxynaphthalene or 2,4,6-trichlorophenol. If a monomer solution is used, polymerization can subsequently be effected by general surface polymerization techniques such as laser induction or temperature increase.

According to the invention, the aftertreatment of the polymer layer applied is effected by drying in commercially available drying installations in air, in a protective gas or in vacuo at temperatures between 0 and 350° C., preferably 30–300° C. and especially preferably between 50 and 250° C.

According to the invention it is possible, in order to achieve thicker polymer layers, for a plurality of application and drying steps to be repeated iteratively.

For the purpose of the invention, the coverage of the piezoelectric crystal after drying is in the range of from 1 ng/cm$^2$ to 100 mg/cm$^2$, preferably from 5 ng/cm$^2$ to 10 mg/cm$^2$ and especially preferably from 10 ng/cm$^2$ to 2 mg/cm$^2$.

After coating, the oscillation capacity of the piezocrystal is checked.

The absorber layer compound applied can be checked by means of (3).

According to the invention, the sensor thus fabricated is exposed to the gas to be tested in a flow cell, with a defined volumetric flow rate. Thermostating is not necessary. The sensor frequency is either evaluated directly or is mixed with a stabilized reference frequency and is then evaluated (plotting of frequency or frequency change against time). The change in signal can, via downstream processors, be converted directly into changes in mass and can be visualized on a display. The sensors are particularly suitable for the detection of ozone, chlorine, bromine, fluorine, hydrogen peroxide and peracids.

The sensors according to the invention can be employed, for example, in the fields of occupational safety and health, immission and emission measurements and as filter monitors.

The invention is explained below in more detail with reference to working examples.

EXAMPLE 1

Commercial HC-18 quartz crystals were removed from their protective housing and dipped into a saturated solution of PPS (MW: 30,000, Tm: 288° C.) in chloronaphthalene at 200° C. Then the sensor was dried at 120° C. for 5 hours in a commercial vacuum drying oven. The oscillation capacity of the coated sensor was tested by means of a transistorized oscillator which causes oscillating quartz crystals to oscillate in parallel resonance between 0.1 and 30 MHz, and a 10 MHz frequency counter (resolution 0.1 Hz) with an interconnectable prescaler and thermostated time base controlled gate.

The frequency change of 8 kHz implies a coverage of 50 μg of PPS on the sensor surface. The sensor was operated for 8 hours in water vapor saturated with $H_2O_2$. The change in frequency was checked every 2 hours. After approximately 2 hours, a linear frequency-time dependence was established, as can be seen from Table 1.

Table 1

Sensor test

Test parameters:

T=120° C., E=Exposure time, $F_O$ (fundamental frequency) =12.7 MHz

Δf: Frequency shift owing to the exposure to the test gas.

1. Exposure of PPS-coated sensors to water vapor Δf=25 Hz (mean value from 4 sensor signals) E=120 min 2. Exposure to hydrogen peroxide vapor (generated from an aqueous solution containing 30% by weight of $H_2O_2$).

Δf=870 Hz (mean value from 4 sensor signals)

E=120 min

3. Exposure to hydrogen peroxide vapor

Δf=166 Hz (mean value from 4 sensor signals)

E=120 min

4. Exposure to hydrogen peroxide vapor

Δf=147 Hz (mean value from 4 sensor signals)

5. Exposure to hydrogen peroxide vapor

Δf=169 Hz (mean value from 4 sensor signals)

6. Exposure to hydrogen peroxide vapor

Δf=160 Hz (mean value from 4 sensor signals)

An ESCA analysis was carried out to verify the chemisorptive action of the sensor. The S 2 p spectrum indicates the partial oxidation of the thioether groups to sulfone linking groups.

EXAMPLE 2

A sensor was fabricated in accordance with Example 1.

Test parameters:

| | |
|---|---|
| Sensor coverage | 50 μg |
| Temperature | 22° C. |
| Fundamental frequency after coating with polymer | 12.7 MHz |
| Ozone concentration | 0.11 cm$^3$ of ozone per m$^3$ of air |
| Flow rate | 0.01 m$^3$/h |
| Duration of the test | 27 hours |

During the test, the sensor shows a linear decrease of frequency against time, with a slope of −2 Hz/h.

EXAMPLE 3

Detection of chlorine

The active detection layer for chlorine was produced by a method similar to that of Example 1. The fundamental frequency of the oscillating quartz crystal used in this case was higher, though, namely 18 MHz.

Test parameters:

| | |
|---|---|
| Fundamental frequency prior to coating with polymer | 18 MHz |
| Frequency change by PPS coverage | 1.9 kHz |
| Sensor coverage | 10 μg of PPS on oscillating quartz crystal |
| Temperature | Room temperature |
| Test gas | Chlorine |
| Flow rate | 0.002 m$^3$/h |
| Duration of test | 10 minutes |

The duration of the test was kept short, given the extremely aggressive atmosphere, to protect the measuring instrument. Over the period of the measurement an overall drop in frequency of 15 kHz was found, the change in frequency being virtually linear with a slope of 1.5 kHz/minute.

We claim:

1. A sensor comprising a piezoelectric crystal with a polyarylene thioether-containing coating.

2. The sensor as claimed in claim 1, wherein the coating contains at least one polyarylene system having repeating units of the formula I,

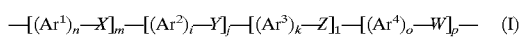

which contain at least one thioether group, in which
- $Ar^1$, $Ar^2$, $Ar^3$ and $Ar^4$ are identical or different aryl systems having from 6 to 18 carbon atoms,
- W, X, Y and Z are identical and different linking groups, selected from the group consisting of $-SO_2-$, $-S-$, $-SO-$, $-O-$, $-CO-$, $-CO_2-$, alkylene or alkylidene having from 1 to 6 carbon atoms and $-NR^1-$, where $R^1$ is an alkyl or alkylide group having from 1 to 6 carbon atoms and at least one linking group must be $-S-$, n, m, i, j, k, l, o, p are, equal or different, integers zero, 1, 2, 3 or 4, their sum having to be at least 2.

3. The sensor as claimed in claim 2, wherein said coating contains a mixture of different polyarylene systems having repeating units of the formula I.

4. The sensor as claimed in claim 2, wherein said polyarylene system of repeating units has a mean molecular weight of from 10,000 to 200,000.

5. The sensor as claimed in claim 2, wherein said polyarylene system of repeating units has a mean molecular weight of from 15,000 to 150,000.

6. The sensor as claimed in claim 1, wherein the coating contains at least one polyarylene having repeating units of the formulae II, III, IV, V, VI, VII or VIII

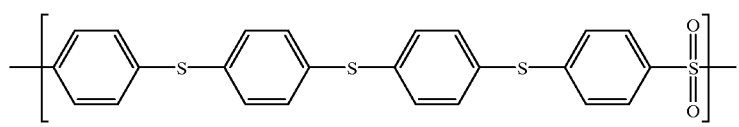

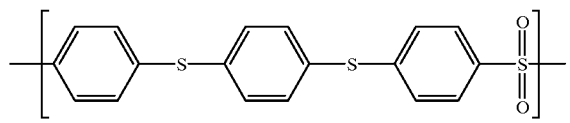

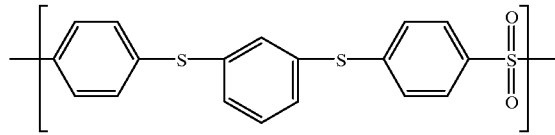

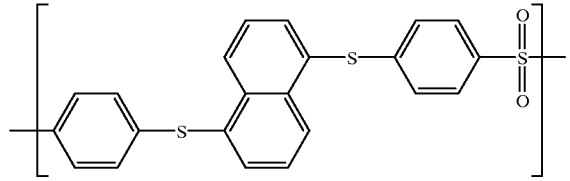

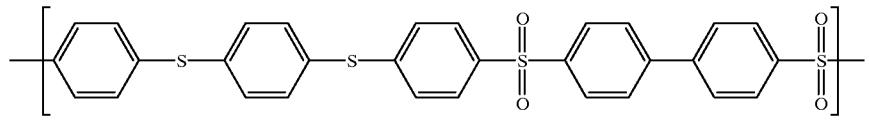

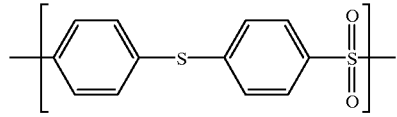

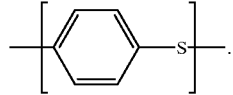

7. The sensor as claimed in claim 6, wherein the coating contains a polyarylene having repeating units of formula VIII.

8. The sensor as claimed in claim 1, wherein the piezoelectric crystal has a fundamental mode in a frequency range of from 20 kHz to 100 MHz.

9. The sensor as claimed in claim 1, wherein the piezoelectric crystal has harmonics in a frequency range of from 1 MHz to 1000 MHz.

10. The sensor as claimed in claim 1,
wherein the piezoelectric crystal employed is an alkaline earth metal titanate, lead-zirconium titanate or quartz.

11. The sensor as claimed in claim 10,
wherein the piezoelectric crystal employed is quartz.

12. A method of using the sensor as claimed in claim 1 for detecting halogen, peroxide-containing compounds or ozone comprising the steps of exposing the sensor to a vapor and detecting any change in frequency of the piezoelectric crystal.

13. A method of using the sensor as claimed in claim 1 in the fields of occupational safety and health, emission measurements and as filter monitors comprising the steps of exposing the sensor to a vapor and detecting any change in frequency of the piezoelectric crystal.

14. The sensor as claimed in claim 1 suitable for detecting halogen, peroxide-containing compounds or ozone.

15. The sensor as claimed in claim 1 suitable for use in the fields of occupational safety and health, emission measurements and as filter monitors.

16. The sensor as claimed in claim 1, wherein said polyarylene system of repeating units has a mean molecular weight of from 10,000 to 200,000.

17. The sensor as claimed in claim 1, wherein said polyarylene system of repeating units has a mean molecular weight of from 15,000 to 150,000.

18. The sensor as claimed in claim 1, wherein the piezoelectric crystal has a fundamental mode in a frequency range of from 0.1 MHz to 50 MHz.

19. The sensor as claimed in claim 1, wherein the piezoelectric crystal has harmonics in a frequency range of from 30 MHz to 500 MHz.

20. The sensor as claimed in claim 1, wherein the piezoelectric crystal is barium titanate.

* * * * *